United States Patent [19]

Majnarich et al.

[11] Patent Number: 5,895,758
[45] Date of Patent: Apr. 20, 1999

[54] **STRAIN OF *LACTOBACILLUS PLANTARUM***

[75] Inventors: John J. Majnarich, Preston, Wash.; Timothy J. O'Brien, Kila, Mont.

[73] Assignee: Bio-Energy Systems, Kalispell, Mont.

[21] Appl. No.: 08/872,269

[22] Filed: Jun. 10, 1997

[51] Int. Cl.⁶ .................... C12N 1/20; A01N 63/00
[52] U.S. Cl. .................... 435/252.9; 424/93.45
[58] Field of Search .................... 435/252.9; 424/93.45

[56] References Cited

U.S. PATENT DOCUMENTS

| | | |
|---|---|---|
| 4,678,773 | 7/1987 | Usami et al. . |
| 5,352,586 | 10/1994 | Dobrogosz et al. . |
| 5,439,678 | 8/1995 | Dobrogosz et al. . |

FOREIGN PATENT DOCUMENTS

| | | |
|---|---|---|
| 1254002 | 8/1986 | U.S.S.R. . |
| 1339124 | 9/1987 | U.S.S.R. . |
| 1678832 | 9/1991 | U.S.S.R. . |

OTHER PUBLICATIONS

Giori et al., "Effect of pH and temperature on the proteolytic activity of Lactic Bacteria", 1985, J Dairy Sci, 68 (9), pp. 2160–2164.

Mollin et al. "Numerical taxonomy of Lactobacillus spp. associated with healthy and disease mucosa of the human intestines", Journal of Applied Bacteriology, 1993, 74 (3), pp. 314–323.

Kang et al., "Immunostimulation effects of cell wall components isolated from Lactobacillus plantarum", J. Microbiol. Biotechnol. 1994, 4 (3), p. 195199.

Carson et al., "Synthesis of 2,3–dideoxynucleosides by enzymatic trans–glycosylation", Biochemical and Biophysical Research Communications, 1988, 155 (2), pp. 829–834.

Cinatl et al., "Invitro anti–human immunodeficiency virus activity of 2,3–dideoxynucleosides and their effect on clonal growth of hemopoietic cells from human bone marrow", Arzneim.—Forsch, 1993, 43(5), pp. 622–625.

J.R. Tennant, *"Evaluation of the Trypan Blue Technique for Determination of Cell Viability,"* Transplantation Articles, Nov. 1964, vol. 2, No. 6, pp. 685–694.

R.I. Geran, N.H. Greenberg, M.M. Macdonald, A.M. Schumacher,and B.J. Abbott, *"Protocols for Screening Chemical Agents and Natural Products Against Animal Tumors and Other Biological Systems,"* Cancer Chemotherapy Reports, Sep. 1972, Part 3, vol. 3, No. 2, pp. 1–103.

*Primary Examiner*—Sandra E. Saucier
*Assistant Examiner*—Vera Afremova
*Attorney, Agent, or Firm*—Blakely, Sokoloff, Taylor & Zafman

[57] ABSTRACT

The invention relates to a biologically pure strain of *L. plantarum, L. plantarum*, OM. The *L. plantarum*, OM strain has proteolytic, anti-viral, anti-retroviral, anti-bacterial, anti-microbial, and anti-tumoral characteristics and uses. Thus, the invention relates to agents having proteolytic, anti-viral, anti-retroviral, anti-bacterial, anti-microbial, and anti-tumoral agents, having the respective capabilities. With respect to its anti-viral capability, the provided strain includes the capacity to screen a pharmaceutical agent to determine whether the pharmaceutical agent has any anti-retrovirus activity. The invention also relates to a nutritional supplement having proteolytic activity and utilizing the *L. plantarum*, OM ATCC 55981 strain.

9 Claims, 1 Drawing Sheet

STRAIN OF *LACTOBACILLUS PLANTARUM*

BACKGROUND OF THE INVENTION

1. Field of the Invention

The present invention relates to the field of microbial genetic engineering and more particularly to a strain of microorganism having, in one embodiment, a proteolytic, anti-viral, anti-bacterial, anti-microbial, and anti-tumoral characteristics and uses.

2. Background of the Invention

Lactobacilli include a large number of non-pathogenic, non-toxic bacteria that play an important role in the health and well being of humans and animals. The metabolic end products of Lactobacillus metabolism include acetic acid, lactic acid and hydrogen peroxide. Certain of these bacteria are known to produce a group of low molecular weight substances, including antibodies, peptides, and peptidoglycans. These low molecular weight substances are useful in reducing growth of spoilage bacteria in fermentable products such as meat, e.g., sausage, salami, etc. Lactobacillus species are added to human and animal food stuffs to preserve them, enhance their flavors, and for probiotic purposes so that these bacteria will become available to the gastrointestinal tract. *Lactobacillus plantarum* strains, for example, are grown commercially in large amounts and used as starter cultures for the commercial preservation of a variety of human and animal foods. *Lactobacillus plantarum* strains are used to preserve meats, vegetables, and dairy products, as well as animal silage. *Lactobacillus acidophilus* strains are grown commercially in large amounts to be added to human (e.g., milk) or animal (feed stuffs) foods as a means of introducing these bacteria into the gastrointestinal tract for probiotic benefits.

Reports on the beneficial effects of Lactobacillus therapy have increased in recent years with findings that dietary Lactobacillus therapy: (i) Affords protection from colon cancer for human populations on Western diets, (ii) reduces the incidents of experimentally induced large bowel tumors in rats, (iii) reduces the fecal concentration of bacterial enzymes known to catalyze the conversion of procarcinogens to proximal carcinogens in humans, and (iv) reduces the serum cholesterol levels in swine.

SUMMARY OF THE INVENTION

According to the invention, a biologically pure strain of *Lactobacillus plantarum*, *Lactobacillus plantarum*, OM is provided. The *L. plantarum*, OM strain has, in one embodiment, proteolytic, anti-viral, anti-retroviral, anti-bacterial, anti-microbial, and anti-tumoral characteristics and uses. Thus, proteolytic, anti-viral, anti-retroviral, anti-bacterial, anti-microbial, and anti-tumoral agents each including *L. plantarum*, OM are provided. With respect to its proteolytic activity, in one embodiment, *L. plantarum*, OM exhibits activity ranges from about 5–15 millimeters. With respect to its anti-viral or anti-retroviral capability, for example, the agent includes the capacity to screen a pharmaceutical agent to determine whether the pharmaceutical agent has any anti-retrovirus activity. A nutritional supplement having proteolytic activity and utilizing the *L. plantarum*, OM strain is also provided.

These and other aspects of the invention will become evident upon reference to the following detailed description and attached drawings.

DETAILED DESCRIPTION OF THE INVENTION

Figure 1:
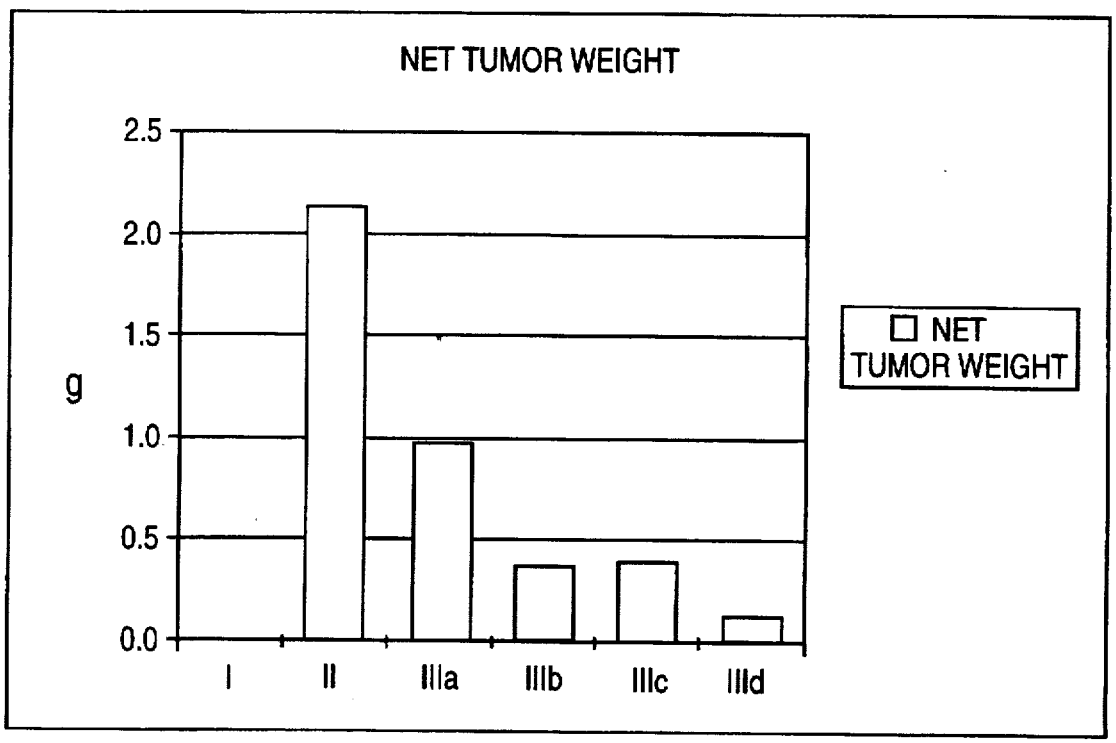
FIG. 1 is a bar graph representation of the net tumor weight for various groups of mice in a study to show the anti-tumoral effect of *L. plantarum*, OM, specifically with the Sarcoma 180 tumor model.

A microorganism grown and harvested as described herein, and exemplified by the properties as described herein is on deposit at the American Type Culture Collection ("ATCC") as of Jun. 5, 1997, under the reference ATCC No. 55981.

A. Biochemical Characterization of *Lactobacillus Plantarum*, OM

*L. plantarum*, OM may be isolated from a fermented meat. The pure isolated culture is inoculated into a deMan, Rogaosa, and Sharpe ("MRS") Agar, then passed again on MRS Agar. A pure isolated culture may be obtained from the ATCC deposit noted above. The second MRS culture is then transferred to API® 50 CHL Lactobacillus medium. API® is a trademark of BioMereinx Vitek, Inc., of Hazelwood, Mo. According to the manufacturer's instructions, the CHL medium is then used to inoculate a series of carbohydrate metabolism tests (API® 50 CHL test strips, BioMereiux Vitek, Inc.) Biochemical reactions of the *L. plantarum*, OM organism with each of the 50 carbohydrates were recorded periodically over 48 hours. The results are tabulated in Table I.

TABLE I

Characteristics of *Lactobacillus plantarum*, OM

| | Expected % Positive | L. plantarum |
|---|---|---|
| Control | 0 | 0 |
| Glycerol | 1 | − |
| Erythritol | 0 | − |
| D Arabinose | 0 | − |
| L Arabinose | 74 | + |
| Ribose | 92 | + |
| D Xylose | 2 | +* |
| Adonitol | 0 | − |
| βMethyl-xyloside | 0 | − |
| Galactose | 92 | + |
| Glucose | 100 | + |
| Fructose | 100 | + |
| Mannose | 100 | + |
| Sarbose | 2 | +* |
| Rhamnose | 33 | +* |
| Dulcitol | 0 | − |
| Inositol | 0 | +* |
| Mannitol | 99 | + |
| Sorbitol | 78 | + |
| Methyl-D-manniside | 55 | + |
| Methyl-D-glucoside | 33 | +* |
| N Acetyl glucosamine | 100 | + |
| Amygdalin | 94 | + |
| Arbutin | 99 | + |
| Esculin | 99 | + |
| Salicin | 99 | + |
| Celloboise | 99 | + |
| Maltose | 100 | + |
| Lactose | 99 | + |
| Melibiose | 94 | + |
| Saccarose | 88 | + |
| Trehalose | 98 | + |
| Inulin | 0 | + |
| Melezitose | 92 | + |
| D-Raffinose | 74 | + |
| Amidon | 7 | + |

TABLE I-continued

Characteristics of *Lactobacillus plantarum*, OM

| | Expected % Positive | L. plantarum |
|---|---|---|
| Glycogen | 7 | +* |
| Xylitol | 0 | + |
| βGentibiose | 99 | + |
| D-Turanose | 62 | + |
| D-Lyxose | 0 | − |
| D-Tagatose | 7 | + |
| D-Fructose | 0 | − |
| L-Fructose | 0 | − |
| D-Arabitol | 36 | + |
| L-Arabitol | 0 | − |
| Gluconate 0 | 0 | − |
| 2-Keto-gluconate | 0 | − |
| 5-Keto-gluconate | 0 | − |

*Represent reactions that are not expected of *L. plantarum*.

The *L. plantarum*, OM organism is maintained at a final pH of 6.3±0.2 on solid MRS agar having a composition of:

| | |
|---|---|
| Bio-Gel Peptone | 10.0g |
| Beef Extract | 8.0g |
| Bio-Yeast Extract | 4.0g |
| Dextrose | 18.5g |
| Dipotassium Phosphate | 2.0g |
| Polysarbate 80 | 1.0g |
| Sodium Acetate | 3.0g |
| Ammonium Citrate | 2.0g |
| Magnesium Sulfate | 0.2g |
| Manganese Sulfate | 0.05g |
| Agar | 13.5g. |

To make working MRS agar media, 62.3 g of powder is suspended in one liter of purified water and mixed thoroughly. The solution is heated with frequent agitation and boiled for one minute to completely dissolve the powder. The media is then sterilized by autoclaving at 121° C. for 15 minutes.

The *L. plantarum*, OM harvested is in the form of straight rods with rounded ends, generally 0.9–1.2 microns wide and 3–8 microns long. The organism occurs singly in pairs or short chains. The biochemical characteristics of *L. plantarum*, OM are illustrated in Table II.

TABLE II

Characteristics of *Lactobacillus plantarum*, OM

| | |
|---|---|
| Mortality | − |
| Gram's Stain | + |
| Casein digested | +* |
| Indole Production | − |
| H₂S | ± |
| Catalase | − |
| Cytochrome | − |
| Benzidine reaction | − |
| Pigment | off white |
| Growth on solid media | + |
| Anaerobic Growth | + |
| Temp. optimum | 30–40° C. |
| pH optimum | 5.5 |

*Expected % positive strains showing a positive reaction after 48 hours at 37° C.

B. Fermentation of *L plantarum*, OM

Having been harvested, the *L. plantarum*, OM organism, is grown anerobically by fermentation. The *L. plantarum*, OM organism is transferred with a sterile loop from a MRS slant and inoculated into a flask containing two liters of MRS broth media. The broth is incubated overnight at 37° C. with stirring to achieve good growth. The medium becomes turbid. The culture is then transferred to a solid medium and Gram stained to confirm the purity of the culture.

A 70 liter LH fermentor is filled with 50 liters of medium having the following recipe:

| | |
|---|---|
| Whey (dry) | 1,000g |
| Cobalt Carbonate | 20g |
| Diammonium Phosphate | 30g |
| Ammonium Hydroxide | 200mL |
| Lactose | 7,000g |

The fermentor and medium are sterilized for 20 minutes at 17 lbs. pressure at 121° C.

The fermentor medium is added to dianodized water and put in the fermentor, diluted to a volume of 50 liters, and sterilized at 17 psi at a 120° C. for 20 minutes. After cooling to room temperature, the inoculum from the 2 liter flask is added aseptically to the 50 liters of medium in the fermentor. The fermentor temperature is brought to 37–38° C. with agitation at 200 rpm and the culture is incubated for 24 hours or until the live organism density is 200–250 million cells per milliliter. The pH of the mixture is 4.5.

Next, a growth stimulator mixture of 2 g of cobalt carbonate, 4 g diammonium phosphate, and 200 mL ammonium hydroxide is added to the medium. The fermentation is continued at 37–38° C. The growth stimulator ingredients are preferably added at four hour intervals for day 2, day 3, and day 4. On day 4, the temperature is decreased to 35° C. On day 5 the temperature is decreased to 28° C. At the end of this period, the medium acidity is 2.0–2.5, with reducing sugars of 1.5%, a pH of 4.1–4.2. The medium has an organism density of 500–900 million cells per milliliter.

Next, the culture solution is concentrated with a Sharples® centrifuge to produce a semi-solid slurry that is 45–50% solids. Sharples is a registered trademark of The Sharples Specialty Company of Philadelphia, Pa. The resulting slurry is freeze-dried to obtain the *L. plantarum*, OM bacterium in a pure, solid phase. The freeze-dried solids are ground in a sterile mill to produce a powder of the organism. The total count of viable *L. plantarum*, OM organism is $10^{10}$–$10^{12}$ cells per gram. This powder may be mixed with food supplements such as vitamins or minerals or food stuffs or an inert carrier (e.g., starch or calcium carbonate or lactose) to provide a nutritional supplement or an agent with, for example, proteolytic anti-retroviral, anti-tumor, and anti-viral capabilities.

*L. plantarum*, OM obtained, for example, from the above fermentation has many useful roles. For example, this *L. plantarum*, OM is proteolytic. Other uses are also described. The following examples demonstrate *L. plantarnum*, OM as a proteolytic, anti-retroviral, anti-tumor, and anti-bacterial anti-microbial agent. Also provided is an example of a nutritional supplement having proteolytic activity and utilizing the *L. plantarum*, OM strain of the invention. The *L plantarum*, OM stain of the invention provides antibacterial activity as some of the conventional *L plantarum* strains. It is not known whether this antibacterial activity is caused by the production of lactic acid (which lowers the pH of the growth medium) or by the production of an antibiotic such as Nicin.

EXAMPLE I.

Proteolytic Activity of *L. plantarum*, OM

The proteolytic activity of *L. plantarum*, OM is assessed by casein hydrolysis on casein agar plates prepared with MRS media. The MRS media is supplemented with 1.5% skim milk powder. The plate when cooled is cut with a 3 millimeters sterile cord borer to make wells in the agar. Into these wells is placed an actively growing *L. plantarum*, OM incubated at 37° C. for 24–48 hours. The incubated plates show a cleared area around the wells, indicating proteolytic activity. The non digested areas have an opaque white appearance.

An alternative method of assessing proteolytic activity is the use of MRS agar to which is added 0.5% Hammerstein casein. Petri plates are poured and allowed to harden. 3 millimeter holes are cut with a sterile cork borer in the agar. The agar holes are filled with actively growing *L. plantarum*, OM culture. The plates are incubated at 37° C. for 24–48 hours. The surface of the plates are then flooded with developer (15% mercuric chloride in 20% hydrochloric acid). The developer is poured off the plates and the size of the clearing is measured.

The proteolytic activity of *L. plantarum*, OM in different experiments ranged from 5–15 millimeters with an average of 8.5 millimeters. The proteolytic activity of conventional *L. plantarum*, on the other hand, is:

| ATCC #4008 | Negligible |
| ATCC #8014 | Negligible |
| ATCC #14917 | Trace (0.1–0.2 mm) |

The proteolytic activity of *L. plantarum*, OM, means this bacterium is useful in the degradation of target proteins. Thus, *L. plantarum*, OM has many uses both in vivo and in vitro for degrading proteins and polypeptides.

EXAMPLE II.
Anti-tumor Activity of *L. plantarum*, OM

This study evaluates the efficacy of *L. plantarum*, OM in reducing tumor size in a Sarcoma 180 tumor model. The Sarcoma 180 tumor model is a recognized model for assessing the efficacy of an agent for anti-tumoral characteristics. The Sarcoma 180 tumor suspension of $2 \times 10^6$ viable cells per 0.1 inoculum was injected into the left hamstring muscle mass of Swiss-Webster mice. The *L. plantarum*, OM was fed to the mice by oral gavage after tumor transplantation. The proceeding paragraphs describe the method and result of this study in detail.

The tumor stock was a Sarcoma 180 which was started in the laboratory from an American Type Culture Collection. This stock culture was passed at weekly intervals as an ascites in non-treated Swiss-Webster mice.

The study used Swiss-Webster mice obtained from Simonsen Laboratories, Gilroy, Calif. Female Swiss-Webster mice were used for testing. The mice were held at a stable temperature and observed daily for signs of disease, stress, injury, and external parasites.

To prepare the inoculum, the ascites fluid from a mouse with a 7–10 day ascites is aspired with a sterile technique. The tumor cells are checked for viability using the trypan-blue staining technique. Once a cell count is established, the tumor cells are diluted with normal saline or phosphate buffered saline to obtain a final concentration of 1 to $2 \times 10^6$ cells/mm$^3$. The final dilution is plated on trypticase soy agar to verify that it is free of contamination. This tumor suspension is injected into the mice.

One tenth (0.1 mL) of the above suspension is inoculated into the left hind leg muscle (hamstring muscle mass) of each mouse. The inoculated mice are placed into one large cage and randomly segregated into groups of six mice. The mice are housed in shoe box cages on wood shavings with free access to water and laboratory chow. The mice are weighed on the day of inoculation, day 7, and day 14 at the time of sacrifice.

Treatment of the mice was initiated the day after transplant and continued for five days. In some experiments, the treatment was not started until day 7 at which time the tumor is palpable. In these instances, the treatment would continue for 5–7 days prior to sacrifice. The latter method demonstrates the effect of a compound on established tumors.

At the end of the approximately 14 day observation period, the mice are sacrificed either by cervical dislocation or ether anesthesia. The skin over the left hind leg is removed to expose the tumor and the leg and tumor are removed at the hip joint. Any residual skin is removed and the legs with tumor are weighed individually. Ten nominal legs (right legs) are prepared in a similar manner and weighed. The mean value of the normal leg is subtracted from the weight of the leg with the tumor to give an estimate of the actual tumor weight.

%Inhibition=[(Mean tumor weight test)/(control Mean tumor weight)]×100

The mice were treated with 500 and 1000 mg per kilogram body weight of *L. plantarum*, OM. The *L. plantarum*, OM was fed to the mice by oral gavage beginning on day six post tumor transplantation for the number of days of treatment outlined below for each group.

Thirty-six mice were placed in six groups (six mice per group). The groups were broken down into the following format:

Group I: The six mice in this group did not receive the challenge or the treatment of the test articles. This group was the negative control, which is a check on general health of the test animals and animal care procedures of the facility.

Group II: The six mice in this group were challenged with the Sarcoma 180 tumor and did not receive any treatment. This group was the positive control. The size of the leg tumors of this group were compared with those of the *L. plantarum*, OM groups in reporting the results of this test.

Group IIIa: The six mice in this group received the Sarcoma 180 tumor on day 0. On day six, these six mice received one treatment of a 500 mg/kg dose of *L. plantarum*, OM in 0.5 mL of solution by oral gavage.

Group IIIb: The six mice in this group received the Sarcoma 180 tumor on day 0. On day six, these six mice received five days of treatment with a daily 500 mg/kg dose of *L. plantarum*, OM in 0.5 mL of solution by oral gavage.

Group IIIc: The six mice in this group received the Sarcoma 180 tumor on day 0. On day six, these six mice received one treatment of a 1000 mg/kg dose of *L. plantarum*, OM in 0.5 mL of solution by oral gavage.

Group IIId: The six mice in this group received the Sarcoma 180 tumor on day 0. On day six, these six mice received five days of treatment with a daily 1000 mg/kg dose of *L. plantarum*, OM in 0.5 mL of solution by oral gavage.

TABLE III

Summary of Experimental Design

| Group | Number of Mice | Challenged with Sarcoma 180 | Lactobacillus plantarum, OM ((mg/Kg) & # days treatment | Mean Leg Weight | Average Body Weight | | |
|---|---|---|---|---|---|---|---|
| | | | | | Week 1 | Week 2 | Week 3 |
| I | Six | no | none | 1.46 | 26.0 | 29.1 | 35.3 |
| II | Six | yes | none | 3.58 | 26.8 | 30.6 | 33.0 |
| IIIa | Six | yes | 500–1 day | 2.43 | 25.8 | 29.6 | 35.0 |
| IIIb | Six | yes | 500–5 days | 1.76 | 26.3 | 30.5 | 36.8 |
| IIIc | Six | yes | 1000–1 day | 1.80 | 26.6 | 30.0 | 33.1 |
| IIId | Six | yes | 1000–5 days | 1.58 | 26.3 | 29.6 | 36.5 |

Table III shows the protocol for each group and the leg weights and weekly average body weight of each mouse for each group. The body weight gains in the treated groups (Groups IIIa–IIId) were similar to the non-tumor group, i.e., Group I, indicating a lack of toxicity at the four doses of test material used.

FIG. 1 is a bar graph of the net tumor weight for each of the different groups. FIG. 1 illustrates that L. plantarum, OM is effective at inhibiting and reducing tumor growth, with the most effective results seen in Group IIId where the mice were gavaged for five days at a dosage of 1000 milligrams per kilogram body weight.

Figure 2:
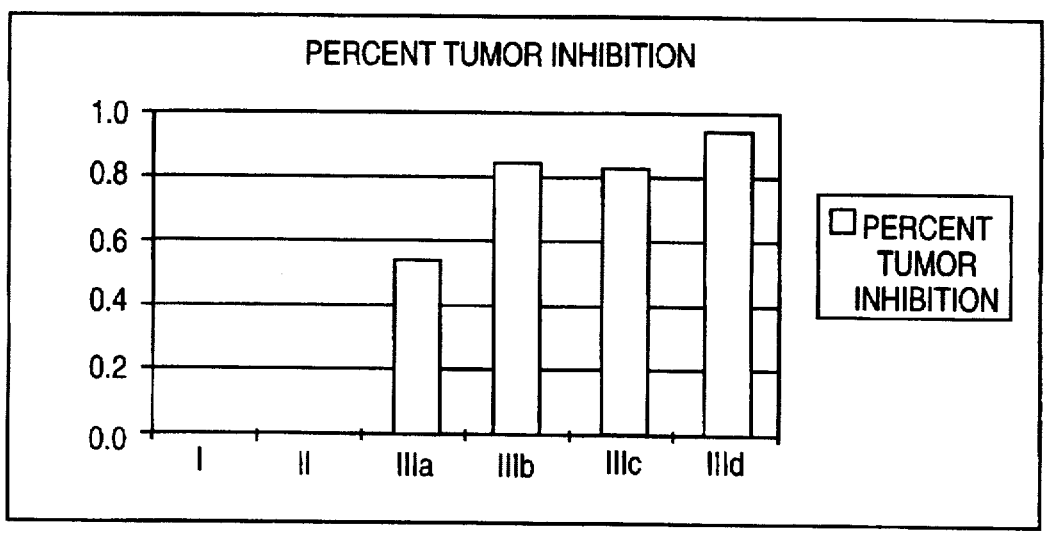
FIG. 2 is a bar graph representation of the percent inhibition of the Sarcoma 180 tumor model in different groups of mice receiving treatment with *L. plantarum*, OM.

FIG. 2 is a bar graph representation of the percent inhibition of the Sarcoma 180 tumor in the different groups receiving treatment with L. plantarum, OM. Using the Sarcoma 180 tumor model and starting treatment after 5 days of tumor growth, one treatment with L. plantarum, OM at 500 milligrams per kilogram body weight gave a 54% inhibition of the tumor. One treatment at 1000 milligrams per kilogram body weight gave an inhibition of 84%. When the mice were gavaged daily for a period of five days following the five days allowed for the tumor growth, at 500 milligrams per kilogram body weight, the inhibition rate was 86% whereas the inhibition was 94% at the 1000 milligrams per kilogram body weight. L. plantarum, OM gave 84% and 94% tumor inhibition in a five day treatment regimen of either 500 or 1000 milligrams per kilogram body weight per day.

The Sarcoma 180 tumor model is an established model for evaluating anti-tumoral agents. The results of L. plantarum, OM on the Sarcoma 180 tumor model demonstrate the efficacy of the provided strain as an anti-tumoral agent. When the mice were gavaged immediately after receiving the tumor, the 84% and 94% tumor inhibition, respectively for 500 milligram and 1000 milligram doses, demonstrate the efficacy and usefulness of L. plantarum, OM for inhibiting tumor growth. The 86% and 94% inhibition, respectively for 500 milligram and 1000 milligram doses, after the tumor was established, demonstrates the efficacy of and usefulness of L. plantarum, OM for treating established tumors.

EXAMPLE III

Effect of L. plantarum, OM on Rauscher Virus

A study was carried out to determine the efficacy and utility of L. plantarum, OM as an anti-retrovirus agent using the Rauscher virus disease model.

EXAMPLE III evaluates the efficacy of L. plantarum, OM, on an established retrovirus disease model. Retroviruses are the cause of considerable human morbidity and mortality. Although these viruses have been known to exist and cause disease in animals for nearly one century, their role as a human pathogen has only been known within the last two decades. Examples of known human retroviruses are human immunodeficiency virus (HIV) and T-lymphotropic virus.

The Rauscher virus is an example of a known animal retrovirus. It was isolated by Dr. Rauscher from the tissue of a leukemic BALB/c mouse in 1962. The virus is a murine leukemia complex and induces leukemia and a rapidly progressive erythrocytic disease in young or older mice of a variety of strains such as BALB/c, DBA/2, Swiss, and C57 BL. Young mice that are injected intraperitoneally ("I.P.") with the virus will develop the symptoms of disease as early as six days and in a few weeks the mice will have palpable spleens and will die in 50 days. The incubation period for tumor development is increased in older mice.

The Rauscher disease model is a very useful and inexpensive technique for the screening of new pharmaceutical agents that have some anti-retrovirus activities. The virus causes formation of erythroid colonies in the spleen of a susceptible mouse. In this model, disease progression can be determined by observing spleen enlargement in infected mice. In healthy non-infected BALB/c mice, the size of the spleen is about 100 milligrams. In an infected mouse, with advanced disease, the spleen size can be more than 2,000 milligrams. Any pharmaceutical agents that alter or interrupt this disease pattern may be considered as anti-retrovirus agents and have a potential for treatment of humans infected with retroviruses.

BALB/c mice weighing 12–15 grams each were used as the test subjects. The mice were obtained from Simonsen Laboratories, Gilroy, CA. The mice were quarantined for a minimum of five days before they were used for testing. The mice were held at a stable temperature and observed daily for signs of disease, stress, injury, and external parasites.

Rauscher Leukemia infected cells (06-000-000) were obtained from Advanced Biotechnologies, Inc. The actual virus used was passed from passage mice.

All groups scheduled to be challenged with the Rauscher virus were challenged on Day 0. Each mouse was injected I.P. with 0.10 mL. The groups were broken down into the following format:

Group I: Twelve mice in this group were not challenged with Rauscher virus on Day 0. The mice were injected (I.P.) with 0.2 mL of physiological saline solution for a duration of five days.

Group II: Twelve mice in this group were challenged with Rauscher virus on Day 0. The mice were injected (I.P.) with 0.2 mL of physiological saline solution for a duration of five days.

Group III-A: Six mice in this group were challenged with Rauscher virus on Day 0. The mice were orally gavaged with 0.5 mL *L. plantarum*, OM solution everyday for a duration of five days. The dosage of *L. plantarum*, OM for this group was 12.5 g/Kg.

Group III-B: Six mice in this group were challenged with Rauscher virus on Day 0. The mice were orally gavaged with 0.5 mL *L. plantarum*, OM solution everyday for a duration of five days. The dosage of *L. plantarum*, OM for this group was 6.25 g/kg.

Group III-C: Six mice in this group were challenged with Rauscher virus on Day 0. The mice were orally gavaged with 0.5 mL *L. plantarum*, OM solution everyday for a duration of five days. The dosage of *L. plantarum*, OM for this group was 1.25 g/kg.

Mortality counts were recorded daily for all groups. The experiment was terminated on day 28 with the weights of all survivors recorded prior to sacrifice. At the termination of the experiment, all spleens were removed and weighed.

TABLE IV

Summary of the Rauscher Model Protocol

| Group | Number of Mice | Saline 0.9% | Test Article | Rauscher Virus | Substance Administration | | | | | |
|---|---|---|---|---|---|---|---|---|---|---|
| | | | | | Day 0 | Day 1 | Day 2 | Day 3 | Day 4 | Day 5 |
| I | 12 | yes | none | no | .1 ml | .5 ml | .5 ml | .5 ml | .5 ml | .5 ml |
| II | 12 | yes | none | yes | Virus | .5 ml | .5 ml | .5 ml | .5 ml | .5 ml |
| III-A | 6 | none | 12.5 g/Kg | yes | Virus | .5 ml | .5 ml | .5 ml | .5 ml | .5 ml |
| III-B | 6 | none | 6.25 g/Kg | yes | Virus | .5 ml | .5 ml | .5 ml | .5 ml | .5 ml |
| III-C | 6 | none | 1.25 g/Kg | yes | Virus | .5 ml | .5 ml | .5 ml | .5 ml | .5 ml |

*All surviving animals sacrificed on Day 28, spleens weighed

Table V shows the mean body and spleen weights of each mouse for all groups. Group I spleen size (100 mg) represents the absence of disease. Group II (positive control) had a massive increase in spleen size (3100 mg) as a result of being infected with the Rauscher virus. The infected groups treated with *L. plantarum*, OM did not demonstrate a massive increase in spleen size.

TABLE V

Summary of the Rauscher Model Protocol

| Group | Mean Final Body Wt. Per Mouse (mmg) | Mean Spleen Weight Per Mouse (mg) |
|---|---|---|
| Group 1 (neg. control) | 21.4 | 108 |
| Group II (pos. control) | 25.0 | 3100 |
| Group III-A | 23.0 | 152 |
| Group III-B | 26.5 | 257 |
| Group III-C | 27.5 | 383 |

The advance of the disease in the retrovirus disease model presented is confirmed by a massive increase in spleen size of the infected mice in the positive control group (Group II, Table V). The treated groups with different doses of *L. plantarum*, OM also developed the disease in decreasing order of dose size. Group IIIa, which received the largest dose (12.5 g/kg) had the best results, with only a slight increase in spleen size.

The results of this study demonstrate that *L. plantarum*, OM has anti-retrovirus activities that are dose related. Accordingly, *L. plantarum*, OM is an effective anti-retrovirus agent with potential for treatment of humans infected with such viruses.

EXAMPLE IV

Effect of *L. plantarum*, OM on Rauscher Virus

This study of the efficacy of *L. plantarum*, OM on the retrovirus Rauscher virus disease model, demonstrates the inhibitory effect as well as the reduction of the virus with *L. plantarum*, OM.

BALB/c mice weighing 12–15 grams each were used as test subjects. The mice were held at a stable temperature and observed daily for signs of disease, stress, injury, and external parasite. Rauscher Leukemia Infected Cells (06-000-000) were obtained from Advanced Biotechnologies, Inc. The actual virus used was passed from passage mice here at Bio Research Laboratories. All groups scheduled to be challenged with the Rauscher virus were challenged on Day 0. Each mouse was injected (I.P.) with 0.25 mL.

Mice were orally given 0.25 mL of *L. plantarum*, OM (10 mg/Kg body weight) for a duration of six days prior to injection and to another group post-injection for 6 days. The groups were broken down into the following format summarized in Table VI:

Group I: Ten mice in this group were not challenged with Rauscher virus on Day 0. The mice were orally given 0.25 mL of physiological saline solution for a duration of six days (Days 1 through 6).

Group II: Ten mice in this group were challenged with Rauscher virus on Day 0. The mice were orally given 0.25 mL of physiological saline solution for a duration of six days (Days 1 through 6).

Group III: The mice were orally pre-treated with 0.25 mL of *L. plantarum*, OM everyday for a duration of six days (Days 1 through 6). Eleven mice in this group were challenged with Rauscher virus on Day 0.

Group IV: Ten mice in this group were challenged with Rauscher virus on Day 0. The mice were orally post-treated with 0.25 mL of *L. plantarum*, OM everyday for a duration of six days (Days 1 through 6).

Mortality counts were recorded daily for all groups. The experiment was terminated on day 28. At the termination of the experiment, all spleens were removed and weighed.

TABLE VI

Summary of the Rauscher Model Protocol

| Group | Number of Mice | Saline 0.9% | Test Article | Rauscher Virus | Substance administration Days 1 through 6 | Day 0 | Days 1 through 6 |
|---|---|---|---|---|---|---|---|
| I | 10 | yes | none | no | none | .25 ml | 0.25 mL saline |
| II | 10 | yes | none | yes | none | .25 ml | 0.25 mL saline |
| III | 11 | none | 0.25 mL | yes | 0.25 mL | .25 ml | none |
| IV | 10 | none | 0.25 mL | yes | none | .25 ml | 0.25 ml |

Table VII shows the mean spleen weights per mouse. Group I spleen size (98.6 mg) represent the absence of disease. Group II had a massive increase in spleen size (3620 mg) as a result of being infected with the Rauscher virus.

Pre-treatment of susceptible mice with *L. plantarum*, OM prevented the increase in spleen weights in this experiment. Treatment following infection also had a marked effect on the spleen weights. One mouse in this group had a spleen weight of 1,120 mg. The other spleen weights in this group ranged from 105–120 mg.

The results of the efficacy of *L. plantarum*, OM on a known retrovirus model demonstrate that *L. plantarum*, OM contains or produces a powerful anti-viral agent. *L. plantarum*, OM can be used as an anti-viral agent itself or may be used to screen other pharmaceutical agents for anti-viral activity, for example, comparing the efficacy of a subject pharmaceutical agent on a known retrovirus model, such as the Rauscher virus model, with the efficacy of *L. plantarum*, OM on the same model.

TABLE VII

Mean Spleen Weights

| Group | Mean Spleen Weight Per Mouse (mg) |
|---|---|
| Group I (neg. control) | 98.6 |
| Group II (pos. control) | 3620 |
| Group III - pre-treatment | 108.8 |
| Group IV - post-treatment | 214.2 |

In the preceding detailed description, the efficacy and utility of the invention is described with reference to specific exemplary uses on known experimental models. It will, however, be evident that, based upon the exemplary embodiments illustrated, the invention has many other characteristics and uses as a proteolytic, anti-viral, anti-retroviral, anti-bacterial, anti-microbial, and anti-tumoral agent. The application and figures are, accordingly, to be regarded in an illustrative rather than a restrictive sense.

What is claimed is:

1. A biologically pure culture of *Lactobacillus plantarum* OM ATCC No. 55981 having proteolytic activity.

2. An agent having anti-tumoral capability comprising a biologically pure culture of *Lactobacillus plantarum* OM ATCC No. 55981.

3. The *Lactobacillus plantarum* OM of claim 2, wherein the anti-tumor capability includes reducing tumor size in a Sarcoma 180 tumor model.

4. An agent having anti-viral capabilities comprising a biologically pure culture of *Lactobacillus plantarum* OM ATCC No. 55981.

5. The agent of claim 4, wherein the anti-viral capability includes the capability to screen a pharmaceutical agent to determine whether the pharmaceutical agent has any anti-retrovirus activity.

6. The agent of claim 4, wherein the anti-viral capability includes anti-retrovirus activity.

7. The agent of claim 4, wherein the anti-viral capability includes the capability to alter the disease pattern for a retrovirus selected from the group consisting of the Rauscher virus, human immunodeficiency virus (HIV) and T-lymphotropic virus.

8. A nutritional supplement having proteolytic activity comprising a biologically pure culture of *Lactobacillus plantarum* OM ATCC No. 55981.

9. The nutritional supplement of claim 8, wherein the *Lactobacillus plantarum* OM strain can be maintained in a human gastrointestinal system.

* * * * *